US006277074B1

(12) United States Patent
Chaturvedi et al.

(10) Patent No.: US 6,277,074 B1
(45) Date of Patent: Aug. 21, 2001

(54) METHOD AND APPARATUS FOR MOTION ESTIMATION WITHIN BIOLOGICAL TISSUE

(75) Inventors: Pawan Chaturvedi, Overland Park; Michael F. Insana, Stilwell; Timothy J. Hall, Shawnee; Yanning Zhu, Lawrence, all of KS (US)

(73) Assignee: University of Kansas Medical Center, Kansas City, KS (US)

( * ) Notice: Subject to any disclaimer, the term of this patent is extended or adjusted under 35 U.S.C. 154(b) by 0 days.

(21) Appl. No.: 09/410,574

(22) Filed: Oct. 1, 1999

Related U.S. Application Data

(60) Provisional application No. 60/102,890, filed on Oct. 2, 1998.

(51) Int. Cl.⁷ .................................................. A61B 8/00
(52) U.S. Cl. ............................................ 600/437; 600/443
(58) Field of Search .................................. 600/437–449, 600/454–456; 73/619–626

(56) References Cited

U.S. PATENT DOCUMENTS 5,113,706 * 5/1992 Pittaro .................................... 73/626
5,787,889 * 8/1998 Edwards et al. ...................... 600/443
6,117,081 * 9/2000 Jago et al. ............................ 600/443

* cited by examiner

Primary Examiner—Marvin M. Lateef
Assistant Examiner—Ali M. Imam
(74) Attorney, Agent, or Firm—Sonnenschein Nath & Rosenthal (57) ABSTRACT

A method for motion estimation within biological tissue is disclosed. The method involves acoustically coupling a transducer to a target biological tissue, which transducer emits an ultrasonic signal and collects the energy backscattered by the target issue. A first set of energy data is collected and stored, then target tissue is axially compressed and a second set of ultrasonic energy data is collected and stored. One of the first and second data sets is warped to account for the anticipated compression forming a warped data set. This warped data set is cross-correlated with the unwarped one of the first and said second data sets to obtain a fine scale displacement of said target biological tissue from the displacement estimated by the warping. This fine scale displacement is summed with the warped data set to obtain a total axial displacement. A gradient of the total axial displacement is taken and used to form a strain image. An apparatus for practicing this method is also disclosed.

1 Claim, 9 Drawing Sheets

NODES
PATCHES

3-D FIRST DATA SET VOLUME

2-D WARPED FIRST DATA SET PIECED TOGETHER FROM THE GENERATED 3-D DISPLACEMENT MAP

FIG. 10

METHOD AND APPARATUS FOR MOTION ESTIMATION WITHIN BIOLOGICAL TISSUE

This application claims benefit of Provisional application Ser. No. 60/102,890 filed Oct. 2, 1998.

BACKGROUND OF THE INVENTION

1. Field of the Invention

The present invention relates generally to a method and apparatus for improving motion estimation within a biological tissue and specifically to local Warping for improving contrast and reducing noise in strain imaging.

2. Background Art

Ultrasonics

It is generally known to use ultrasonics for non-invasive imaging of soft biological tissue. An acoustic transducer is used as both a transmitter and receiver of sound pulses in the 1–50 MHz frequency range. The transducer is used in a pulse-echo system where the transducer converts between electrical and acoustic energy to transmit and receive sound pulse to and from the target tissue. Received signals are translated by a computer to produce an image.

Elastography

A technique called elastography was developed in concert with ultrasonics in order to detect inhomogeneities or stiff regions within soft biological tissues. Elastography is a remote sensing technique for imaging elastic properties of biological tissues. Elastograms are formed by comparing two-dimensional arrays of RF echo signals recorded before and after applying a weak compression to the biological tissue. When the force is applied to the surface of the biological tissue, a stress field is generated that deforms the tissue volume within. An elastogram is an image of the resulting deformation or strain of the associated tissue. To create an elastogram, a displacement field is estimated from windowed segments of ultrasonic echo signals acquired before and after a weak compressive force is applied along the axis of the sound beam. Strain Images are formed by taking the gradient of the displacement map obtained via comparison between ultrasound RF echo fields. The displacement deformation is estimated by cross correlating these echo signals. The cross correlation between the amplitude line (A-line) segments in the pre-compression data and the corresponding A-line segments in the post-compression data is calculated. The lag at the peak of the cross correlation reveals the displacement of the tissue caused by compression.

In principle, any diagnostic imaging modality can be used to estimate this displacement. In practice, however, ultrasound and magnetic resonance imaging provide the best motion estimations. Local tissue displacement is the fundamental measurement of strain imaging that determines visibility of targets. This procedure is useful because the motion of a stiff region, like a tumor under compression, is different than motion of normal soft biological tissue under compression. This difference is reflected in relative changes in ultrasonic signals recorded before and after compression.

1-D Companding

Accurate estimates of displacement using only the cross correlation method described above require there to be little strain over the echo segment. Unfortunately, the deformation of biological tissue is typically very complex and large decorrelation errors persist. An early method for reducing some decorrelation errors involved temporally stretching the compressed echo field globally by the amount of the physical compression prior to cross correlation. Because cross correlation methods assume there is only rigid-body motion over the duration of the data window, stretching signals by the applied strain conditions the data to better satisfy this critical assumption. This global temporal stretching is known in the art of radar imaging and sound recording.

Temporal stretching, however, fails to remove significant decorrelation errors because when a nearly incompressible material such as a biological tissue is compressed in one direction, for example, along the axis of the ultrasonic beam, it necessarily bulges in directions not axial to the beam. This causes the echo field to be distorted in three dimensions.

It is known in the art of radar imaging and sound recording to use a technique called 1-D companding to reduce decorrelation errors in one direction in an attempt to improve image quality. Just like temporal stretching, 1-D companding is a pre-processing technique applied to the pre or post-compression data prior to cross correlation. 1-D companding refers to a spatially-variable signal scaling along the axis of the beam through not just temporal stretching, but compression and expansion of the signal by an estimation of the applied strain to that signal. This technique attempts to reduce estimation noise by restoring coherence between the waveforms to be cross-correlated. The improvement in image noise using 1-D companding, however, is highly dependent on the duration of the data window, the elastic heterogeneity of the medium, and the amount of applied strain.

Accordingly, five main problems exist with the current acoustic motion estimation and strain imaging techniques: 1) Noise; 2) Contrast; 3) Out of Plane Displacement; 4) Shear Motion; and 5) Rotational Motion.

Noise

Noise is a consequence of the disagreement between the pre and post-compression echo fields strain (lack of coherence). Noise increases with the amount of applied compression. Two main reasons for this increase are: 1) the windows used for cross correlation analysis may contain significant strain due to the size of the window; and 2) the segment of the biological tissue under investigation may rotate, shear and/or move laterally from its original location so that the corresponding A-lines in pre and post-compression images no longer contain correlated data from the same region of the object. Correspondingly, it is well known in the art to compress biological tissue only a small percentage (typically less than 1%) of its total height to maintain strain noise at an acceptable level.

Contrast

Contrast is the difference in brightness between the target within the biological tissue and the background of the biological tissue itself. An increase in compression increases the contrast, which allows for better viewing of the target in the strain image. As noted above, however, increased compression also increases noise, which distorts the strain image. Also, as noted above, compression is generally limited to 1% of the targets total height in order to limit noise. Limiting compression also limits contrast making abnormal tissue more difficult to detect.

Out of Plane Displacement, Shear and Rotational Motion

Out of plane displacement occurs when the target moves perpendicularly out of the scan plane upon compression. The directions perpendicular to the scan plane, parallel with the ultrasound beam, and perpendicular to the beam in the scan plane are referred to as elevational, axial, and lateral respectively. Shear motion occurs when motion in one direction, e.g., axially, depends on the position in another direction, e.g., laterally. Rotational motion occurs when the target rotates away from its original orientation either within or out of the scan plane. While there are many elements on a 1-D linear array transducer for sending pulses and receiving echoes in the lateral direction, there is only one row of elements on the transducer in the elevational direction. Consequently, a target that may have moved in the elevational direction with respect to the transducer can not be tracked because the post-compression echo field does not contain any data from such a target; resulting in axial decorrelation. Similarly, shear and rotation result in greater decorrelation noise when simple techniques such as 1-D stretching and 1-D cross correlation are used.

Unfortunately, biological tissues do not move simply in only one dimension when compressed. Correspondingly, the known use of temporal stretching and 1-D companding is insufficient to avoid decorrelation errors. Extending the concept of global temporal stretching to 2-D and 3-D is not viable because it is rare that the biological tissue is homogeneous and incompressible at all spatial scales as required.

Accordingly, it is a primary object of the present invention to provide a method and apparatus for improving motion estimation within a biological tissue.

It is another object of the present invention to provide a method and apparatus for improving strain imaging of a biological tissue regardless of the source of the applied strain.

It is another object of the present invention to provide a method and apparatus for detecting and compensating for out of plane displacement, rotational motion and shear in motion estimation and strain imaging in biological tissue.

It is another object of the present invention to provide a method and apparatus for reducing noise in acoustic strain imaging.

It is yet another object of the present invention to provide a method and apparatus for increasing contrast in acoustic strain imaging.

SUMMARY OF THE INVENTION

The improved method and apparatus of the present invention for motion estimation within a biological tissue and strain imaging includes Warping as well as 2-D, 2.5-D, and 3-D Local Linear Warping to improve motion estimation and strain imaging. The invention is described as applied to strain imaging, however, this method and apparatus is equally applicable to other forms of displacement and motion estimation within a biological tissue because displacement, or motion estimation is a vital aspect of this process.

Warping

This inventive technique identifies and accounts for three dimensional bilinear motion of objects within a biological tissue, including rotational motion and shear, by deforming the data prior to cross correlation. Accordingly, noise previously introduced in prior art techniques during cross correlation is significantly diminished in the present invention allowing the user to apply a greater compressive force resulting in greater contrast in the final image when this technique is used in strain imaging for example. The biological tissue, typically in vivo, is positioned such that a compressive force can be applied. Pre-compression data is collected and stored in the processing computer in the form of A-lines as a first data set. Next, a static compressive force is applied to the biological tissue and maintained while post-compression data is taken and stored in the processing computer as another set of A-lines as a second data set. While the present invention is described with reference to an exogenous force, it is contemplated that various types of compressive forces including endogenous forces due to breathing, blood pressure, etc., may be used to apply a compression to the biological tissue. The compressive force may be internal or external. Then one collected data set is Warped to account for the physical compression and create a closer match with the other data set.

Warping is performed through the application of a modified deformable mesh model. The deformable model detects and tracks gross objects within an image. In motion estimation and strain imaging in biological tissues, it is necessary to track every pixel in the image in order to accurately estimate the displacement of the biological tissue caused by a physical compression. Accordingly, the present invention modifies the deformable model to perform motion tracking for every pixel. A data set or echo field is divided into small patches and motion for each patch is estimated. Independent bilinear transformations, which compensate for motions such as translation, scaling, rotation and shear are allowed in each patch. In this way, the global motion of the compressed material is estimated in a piece-wise manner.

Finally, 1-D cross correlation along the ultrasound beam is performed to estimate the fine scale motion within the biological tissue. The sum of this displacement and the large-scale motion introduced (or subtracted) during Warping provides the total displacement within the biological tissue. An image is created by taking the spatial gradient of the displacement in the desired direction or, in this case, along the ultrasound beam. In this way, all large-scale linear motion as well as shearing and rotation is detected and accounted for prior to cross correlation. This reduces the displacement estimation noise and allows for greater compression (up to 10%) and, correspondingly, greater contrast.

3-D Local Linear Warping

When the biological tissue being scanned is generally homogeneous and not overly complex, like breast tissue in a young patient or early stage cancer, rotational motion and shear are minimal upon compression and, therefore, compensating for rotation or shear is not necessary. The presence of complex biological tissue can frequently be detected by examining the ultrasound scan while recording the pre and post-compression echo fields. In this case, a more computationally efficient version of Warping called 3-D Local Linear Warping may be employed. 3-D Local Linear Warping is a subset of Warping in which translation and scaling motions are accounted for. 3-D Local Linear Warping may be applied to either the first or second data set prior to cross correlation. While either data set may be warped, the process of warping the first data set to account for the physical compression will be described.

Similar to the Warping technique previously described, the biological tissue sample is scanned by the transducer and a first, or pre-compression, data set as well as a second, or post-compression, data set is acquired and stored. In 3-D Local Linear Warping, the first data set is a three-dimensional volume comprised of several scan planes. Only one scan plane, forming a two dimensional data set, for the second data set is required. The method of data collection is the same as with Warping.

Once the first and second data sets are stored, 3-D Local Linear Warping is performed. First, a two dimensional mesh is created on the second data set and each A-line in that data set is stretched along the ultrasound beam by the amount of compression applied to improve processing speed. Next, a two-dimensional data kernel is selected in the second data set and compared to data in a three-dimensional search region of the first data set. Then, the displacement for each pixel is calculated and a three-dimensional displacement map that describes the physical deformation is created. From this displacement map, a two dimensional pre-compression image is pieced together from the first data set so that the resulting data set is deformed similar to the physical compression.

In this way, all large-scale linear motion, including out of plane displacement, is detected and accounted for prior to cross correlation. This reduces the displacement estimation noise and allows for greater compression and, correspondingly, greater contrast.

2.5-D Local Linear Warping

When the motion of a biological tissue like muscles is naturally constrained by a bone or other internal structure, the biological tissue's motion can be assumed to be in a plane different from but approximately parallel to the ultrasound scan plane, 2.5-D Local Linear Warping may be used. 2.5-D Local Linear Warping is effective when all data in a single compression plane generally moves to a single post-compression scan plane. Just like Warping, 2.5-D Local Linear Warping may be applied to either the first or second data set prior to cross correlation. While either data set can be warped, the process of warping the first data set to account for the physical compression will be described.

Similar to the Warping technique and the 3-D Local Linear Warping technique, the biological tissue is scanned by the transducer and a first, or pre-compression, data set as well as a second, or post-compression, data set is acquired and stored. In 2.5-D Local Linear Warping, the first data set is a three-dimensional volume comprised of several scan planes. Only one scan plane, forming a two dimensional data set, for the second data set is required. The method of data collection is the same as with Warping and 3-D Local Linear Warping.

Once the first and second data sets are stored, 2.5-D Local Linear Warping is performed. First, a two dimensional mesh is created on the second data set and each A-line in that data set is stretched by the amount of applied compression. Next, the pre-compression scan plane from which data has moved to the acquired post-compression scan plane is identified. A two-dimensional data kernel is selected in the second data set and compared to data in a two-dimensional search region of the previously identified pre-compression scan plane in the first data set. Then, the local displacement for each pixel is calculated and the displacement is found.

Accordingly, the first data set is deformed such that the deformation in the resulting echo field is similar to the physical compression recorded in the second data set and 2.5-D Local Linear Warping is complete. In this way, any large-scale linear motion of the biological tissue from the selected pre-compression scan plane into a post-compression scan plane is detected and accounted for prior to cross correlation. This reduces the displacement estimation noise and allows for greater compression and, correspondingly, greater contrast.

2-D Local Linear Warping

When no naturally occurring constraint exists, but the motion of the biological tissue to be scanned, like breast tissue, can be artificially restricted to a single ultrasound plane by the imposition of suitable physical boundary conditions in all other planes, then 2-D Local Linear Warping may be used. Because the motion is confined to a single plane, only single scan planes need be recorded for both pre and post-compression. Data is collected and stored in the same manner as with Warping, 3-D Local linear Warping and 2.5-D Local Linear Warping.

Once the first and second data sets are stored, 2-D Local Linear Warping is performed. First, a two dimensional mesh is created on the second data set and each A-line in the second data set is stretched by the amount of applied compression. Next, a two-dimensional data kernel is selected in the second data set and compared to data in a two-dimensional search region of the pre-compression scan plane in the first data set. Then, the local displacement for each pixel is calculated. Accordingly, the first data set is deformed such that the deformation in the resulting echo field is similar to the physical compression recorded in the second data set and 2-D Local Linear Warping is complete. In this way, any large-scale linear motion of the target object within the scan plane is detected and accounted for prior to cross correlation. This reduces the displacement estimation noise and allows for greater compression and, correspondingly, greater contrast.

Global Warping methods may be applied prior to the finer process of Local Warping described above in all methods presented to increase processing speed but will not improve image quality and are, therefore, not necessary. Temporal stretching is equivalent to global scaling along the ultrasound beam.

BEST MODES OF CARRYING OUT THE INVENTION

While the present invention may be embodied in many different forms there is shown in the drawings and discussed herein one specific embodiment and specific fabrication method with the understanding that the present disclosure is to be considered only as an exemplification of the principles of the invention and is not intended to limit the invention to the embodiments illustrated.

Warping

Figure 1:
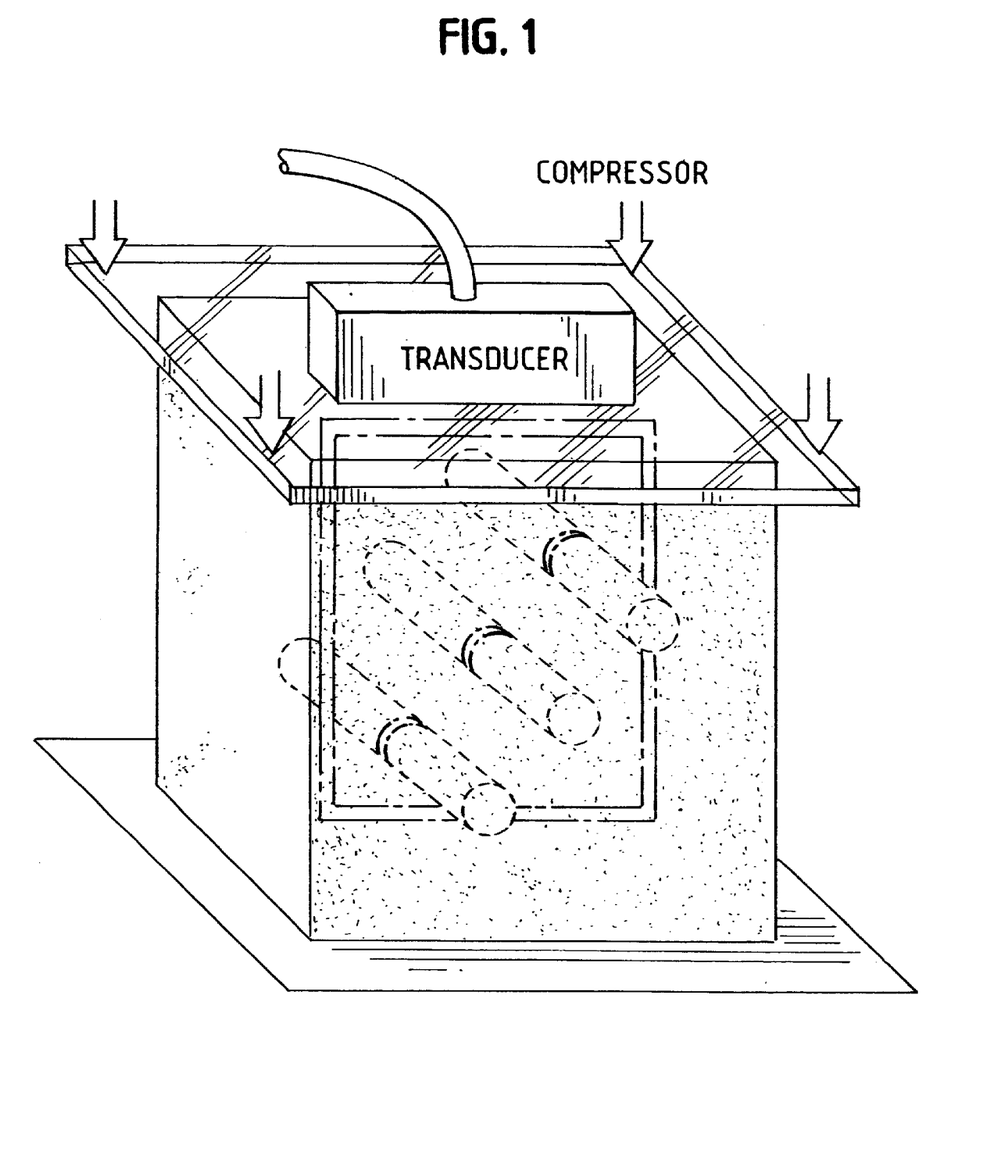
FIG. 1 is a front perspective view of the scanning apparatus of the present invention compressing a gelatin phantom.

As shown in FIG. 1, a transducer having a rectangular grid of sensors is flush mounted to a planar compressor surface. While a two dimensional planar array transducer is preferred, a transducer having sensors in concentric circles or a linear array transducer may be used. If only a one dimensional detector array is available, a plurality of pre-compression images or post-compression images, or both may be taken to obtain the three dimensional data set, if required, around the target object. All the data from the multiple scans is then combined to form the data sets.

In the preferred embodiment, the planar array transducer is an f/2 system with an A-line density of 5 per millimeter and emits broadband ultrasonic waves with a center frequency of 5 MHz and a bandwidth of 4 MHz and records 200 echo waveforms for a 40 mm×40 mm region at a sampling rate of 45 samples per microsecond. While this is preferred, any acceptable emission/recording specifications may be used. Also, while the Warping technique is described in a preferred embodiment in conjunction with ultrasound, Warping may also be used to improve image quality in magnetic resonance imaging, x-ray imaging and other electromagnetic diagnostic imaging techniques.

Figure 2:
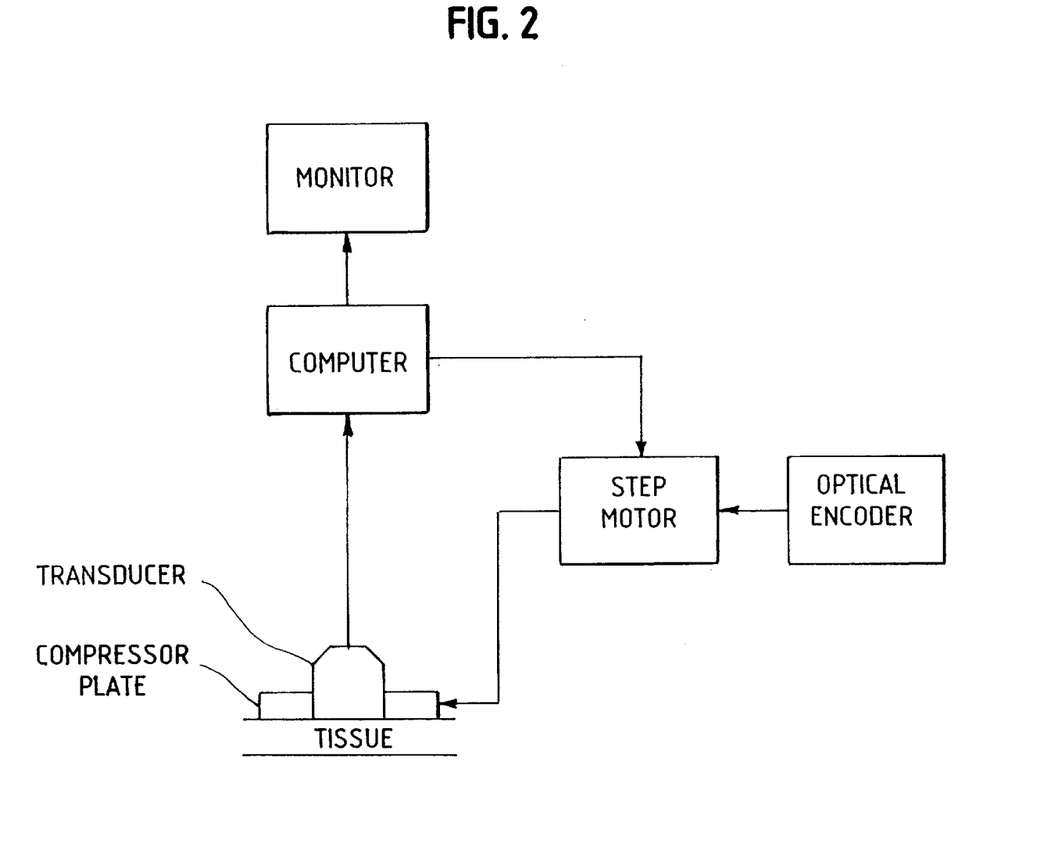
FIG. 2 is block diagram showing an embodiment of the apparatus in which a compressor plate having a flush mounted transducer is coupled with a biological tissue for the purpose of strain imaging.

As shown in FIG. 1, the planar compressor is mounted in the x, y plane to be in contact with the biological tissue depicted as a gelatin phantom. While it is preferred to use a planar compressor, the transducer, a human hand, or any suitable device may serve to maintain an axial compression on the target object. As shown in FIG. 2, the compressor may be moved along the z-axis by a computer controlled stepper motor having it's position monitored by an optical encoder.

As shown in FIG. 2, the transducer is preferably connected for the purpose of signal processing and image formation to a Digital Equipment Corporation alpha workstation, although any general-purpose computer and monitor may be used. Signal processing and image formation is conducted off-line on the computer, although such processing could be conducted on-line by using any dedicated system such as a digital signal processor. As shown in FIG. 1, the transducer scans the biological tissue for a pre-compression image (U) by emitting ultrasonic pulses that travel through the biological tissue. These ultrasonic pulses are scattered within the biological tissue and the back-scattered energy is recorded by the sensors in the transducer and stored in the processing computer as A-lines. This group of A-lines combines to form the first data set. Thus, the pre-compression echo field is stored as the first data set in the computer for later processing.

Figure 7:
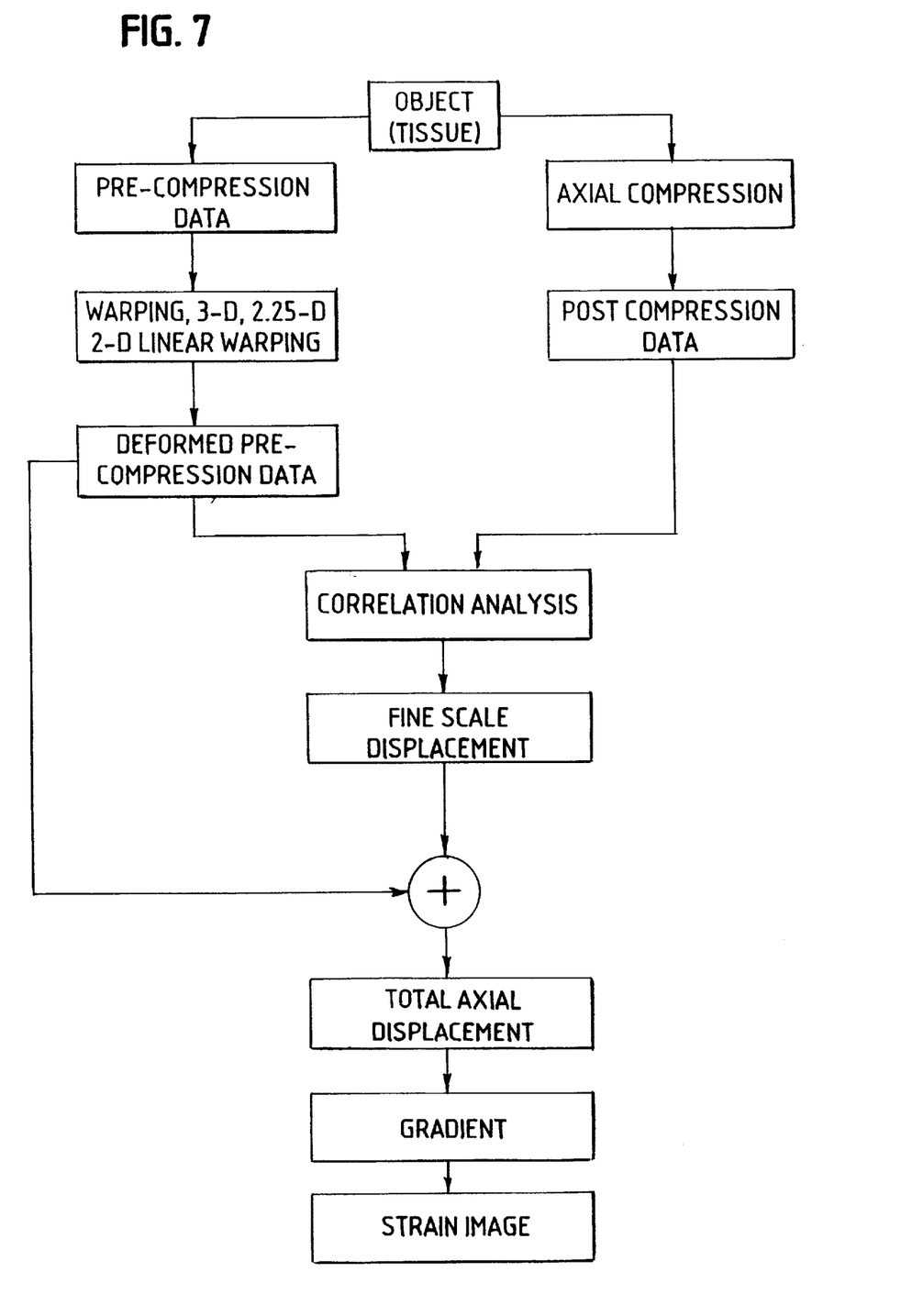
FIG. 7 is a block diagram showing the image formation process of the present invention.

Next, as shown in FIG. 7, an axial compression is applied to the biological tissue. Compressions up to 10% of the biological tissue's height may be applied to obtain better contrast in the strain image. The user inputs a desired compression into the computer, which passes along the instruction to the computer-controlled stepper motor. The computer controlled stepper motor in turn moves the planar compressor along the z-axis to compress the biological tissue the desired amount. After compression, the transducer scans for a post-compression image (C) generating a second data set in the same manner as the first data set. When multiple pre or post-compression scan planes are desired, this process is repeated the requisite number of times with successive scans taken by translating the transducer by the desired amount elevationally.

To perform Warping, a modified deformable mesh model is applied. An active contour or "snake" model is used to detect and track lines and edges in an image. A snake is an energy-minimizing spline. The energy has three components: internal energy, image energy, and external energy. The internal or spline energy maintains the elasticity properties of the spline. The image energy provides a resisting forcing. This force is stronger on the line and edge locations of the image. The external energy pulls or pushes the spline in order to search for the image features (lines and edges). The advantage of this method is that while maintaining the elasticity properties of the spline, it is also deformed on the image and actively searches for the desired features. Because strain imaging requires tracking not just single image features like lines and edges but surface images, this method was expanded to meshes and shells and called a deformable mesh model. The above method aims to detect and track gross objects within an image. In strain imaging, in order to obtain an accurate estimate of the displacement caused by the physical compression throughout the biological tissue, it is necessary to track every pixel on the image.

Figure 3:
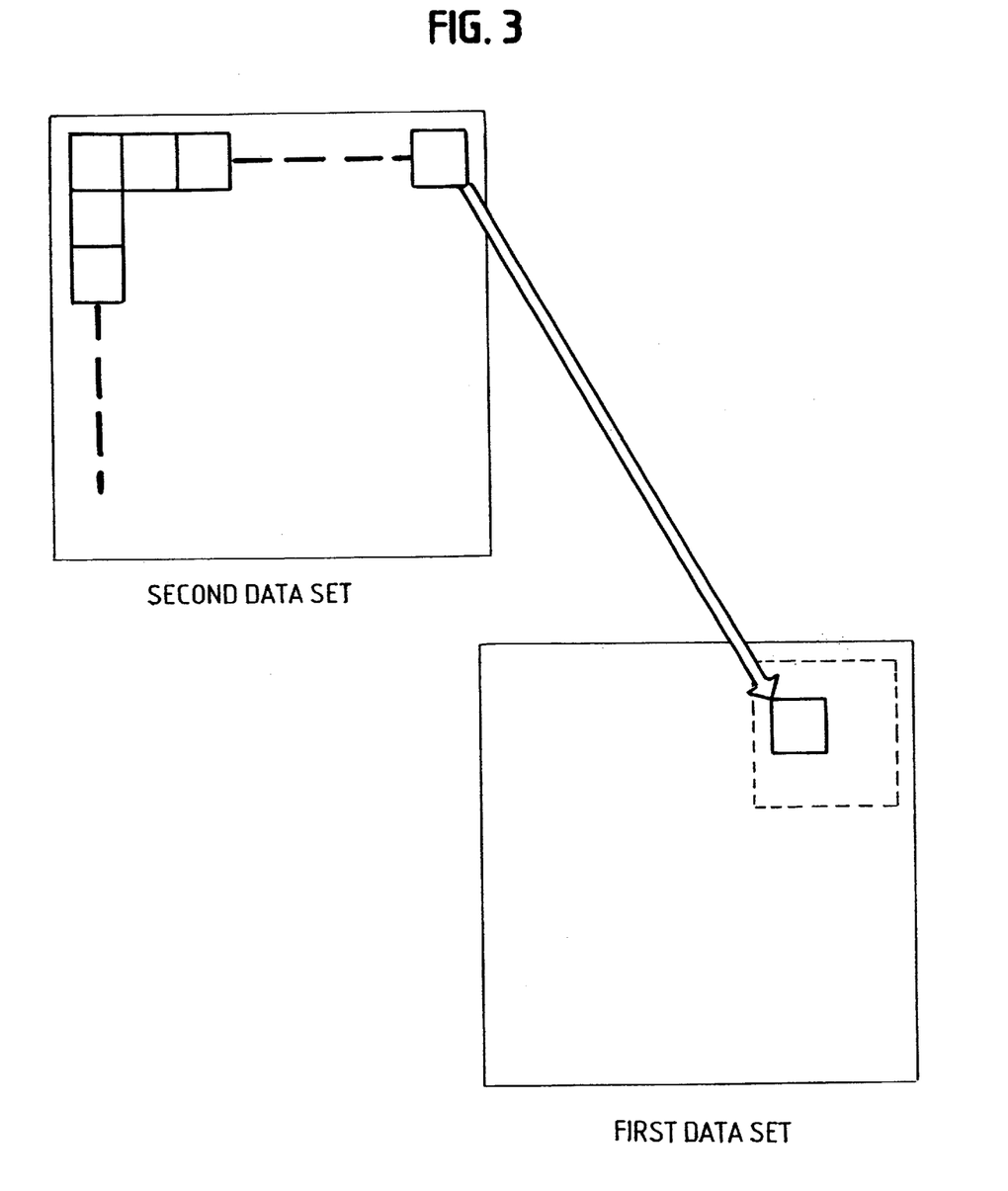
FIG. 3 is a representation of local linear warping of the present invention.

Accordingly, as shown in FIG. 3, the deformable mesh model is modified for performing motion tracking for every pixel and called the Deformable Mesh Ultrasound Strain Imaging Algorithm (DMUSIA). The biological tissue is divided into small patches and motion for each patch is estimated. Independent bilinear transformations are performed within each patch. In this manner, the global motion of the compressed biological tissue is estimated in a piecewise manner. We denote the first and second data sets as U and C, respectively. It is preferred to use DMUSIA to Warp U to match the physical deformation recorded by C; however, C could be Warped to remove said physical deformation. The Warped version of U is denoted as W. The coarse axial displacement estimated from W is denoted as $D_w$. C and U are cross correlated to obtain the fine-scale residual displacement called $D_c$. The total axial displacement is then calculated as $D_t = D_w + D_c$ and the strain is then calculated as:

$$S = \frac{\partial}{\partial y} D_t \tag{1}$$

To represent orthogonal axes, x, y, and z are used as the lateral, axial, and elevational directions, respectively. An overview of DMUSIA, separated into five modules (A–F), is provided in FIG. 6.

Figure 4:
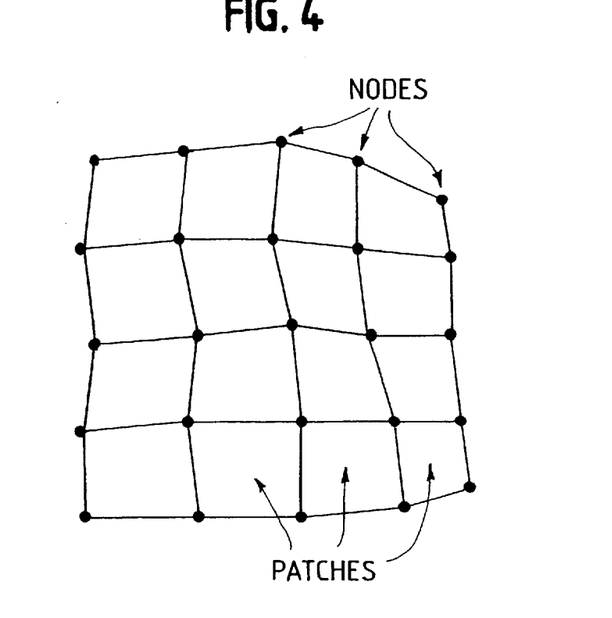
FIG. 4 is a quadrilateral mesh representation of warping of the present invention.
Figure 6:
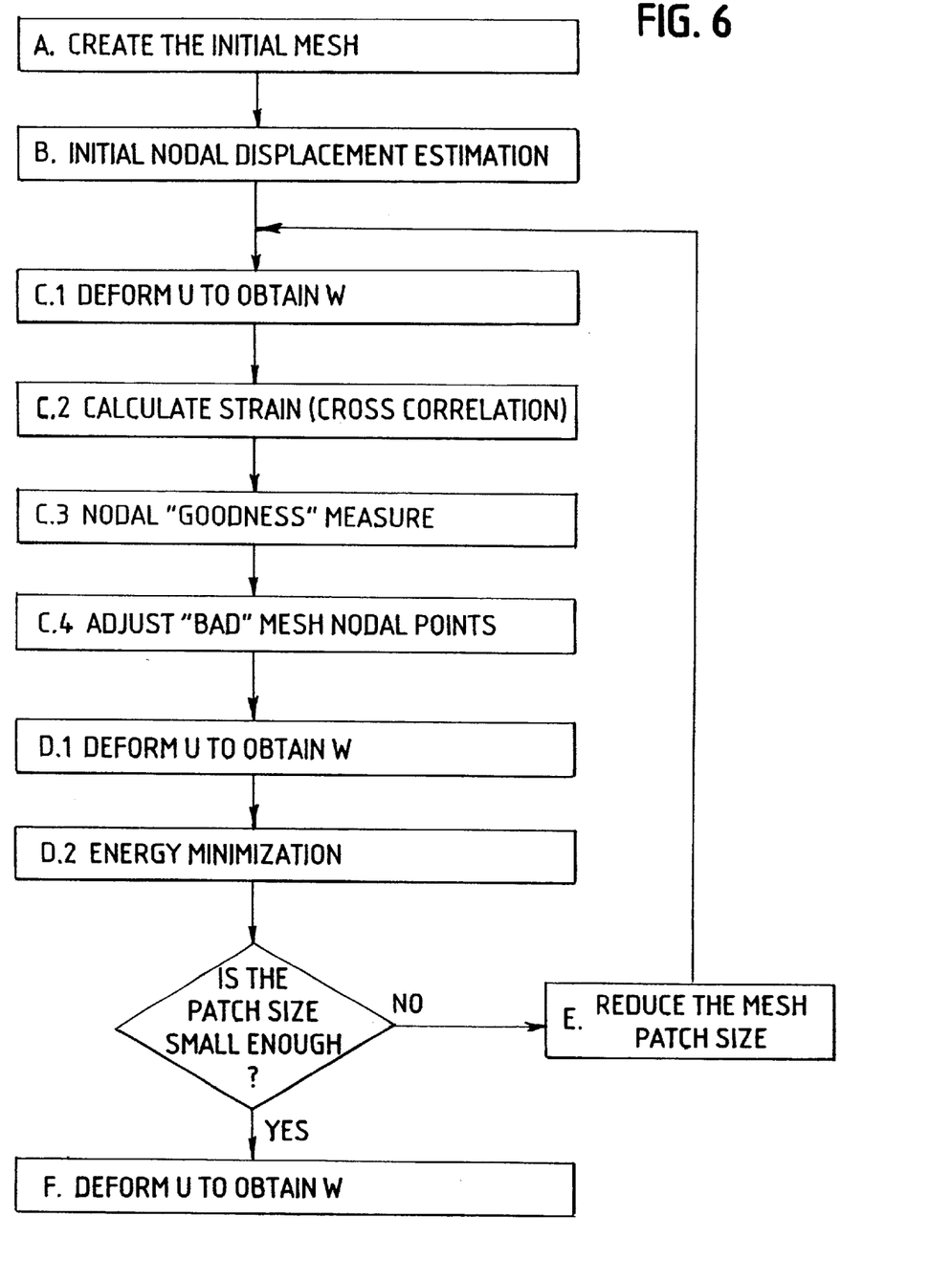
FIG. 6 is a block diagram showing Warping of the present invention.

As shown in FIG. 6, first, the initial mesh is generated and placed on U in module A. Independent bilinear transformations are performed in each patch. As shown in FIG. 4, a mesh is defined by a collection of nodes placed on top of a two-dimensional echo field. A row vector $n = [n_1, n_2]$ is used to identify a node where $n_1$ and $n_2$ are the row and column indices of the node, respectively; $L_x(n)$ and $L_y(n)$ are the x and y coordinates of the node, respectively. Adjacent nodal points are connected to form closed areas called patches. A patch is denoted as $p = [p_1, p_2]$ where $p_1$ and $p_2$ are the row and column indices of the patch, respectively. While the shape of the patch can be any appropriate shape like a triangle, in the preferred embodiment of this invention, a quadrilateral mesh is used. If a signal is geometrically inside a patch, then it belongs to that patch. As such, a patch can be considered a collection of signal points.

Figure 5:
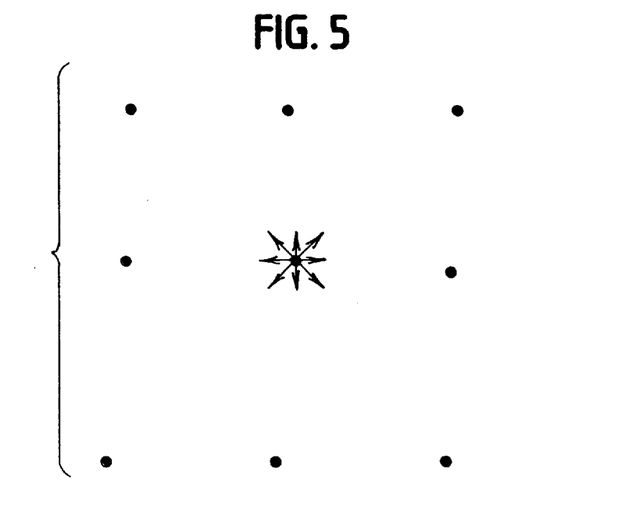
FIG. 5 is a nodal perturbing directions representative of the present invention.

As shown in FIG. 4 and FIG. 5, the locations of the nodes, n, on the initial mesh will be changed on C because of the compression. The displaced nodes form the deformed mesh on C and are denoted by $$n' = [n'_i, n'_j].$$

Adjacent nodes of the deformed mesh are connected the same way as the initial mesh obtaining the quadrilateral patches of the deformed mesh denoted as $$p' = [p'_l, p'_j].$$

Accordingly, the effect of the compression is to displace n to n' and p to p'.

Second, as shown in FIG. 6, in module B, an initial estimate of the displacement caused by the physical compression is made and applied to the first data set using a block matching algorithm. This estimate is fine-tuned in later processing. Module C overcomes an associated problem of local minima. This problem occurs when the block matching algorithm used in module B places some nodes on the deformed mesh far away from their expected locations. When the energy minimization described below occurs, these nodes would need to travel relatively long distances toward their true locations and past several local minima. Consequently, the energy function may not behave properly and can become 'trapped' in locally low energy values not corresponding to the desired true global minima. Module C avoids this problem by placing all nodes on the deformed mesh close to their true locations. First, the bilinear transformation is applied to all echo samples in U based on nodal displacement estimated in module B to obtain W. An assumption is made that all echo samples in U are spatially transformed to a patch in C via a single transformation matrix. The choice of the spatial transformation is bilinear. While any transformation, commonly including affine and perspective, may be used in the preferred embodiment bilinear transformations are used. The two-dimensional bilinear transformation can be written as:

$$x' = a_1 x + a_2 y + a_3 \quad (2)$$

$$y' = a_4 x + a_5 y + a_6 \quad (3)$$

These equations describe any combination of motions involving translation, rotation, scaling, and shearing. The bilinear transformation has eight degrees of freedom. Accordingly, the transformation coefficients are calculated using coordinates of four nodes of the corresponding patch pair on the initial and deformed meshes. After cross-correlating C and W, and estimating the total displacement, the axial strain is computed by taking a spatial gradient of the displacement field along the ultrasound beam. This is not done to achieve a final result, but instead serves to allow the smoothness of the local strain to be examined so that nodes placed far from their true locations can be detected using the 'goodness measure.' In the preferred embodiment, three criteria are used to measure the goodness of the node placement. The criteria are the absolute value of the strain; the first order difference of the strain; and the second order difference of the strain. The goodness measure at the node n' is denoted g(n') and defined as:

$$g(n') = \begin{cases} 1 & \text{if } |s(x_n, y_n)| \le t_1 \text{ and } |\text{diff}(s(x_n, y_n))| \le t_2 \text{ and} \\ & |\text{diff}(\text{diff}(s(x_n, y_n)))| \le t_3 \\ 0 & \text{otherwise} \end{cases} \quad (4)$$

where $$\text{diff}(s(x_n, y_n)) = s(x_n, y_n) - s(x_n, y_{n-1}) \text{ and } \text{diff}(\text{diff}(s(x_n, y_n))) = \text{diff}(s(x_n, y_n)) - \text{diff}(s(x_n, y_{n-1})). \quad (5)$$

Here, $t_1$, t2, t3 are constant thresholds. The values of the constants are chosen empirically. Constant $t_1$ is determined from the amount of physical compression coupled with the maximum level of strain allowed. For example, if we apply 5% compression with a maximum strain of 10%, then $t_1$ is chosen to be 1.1*0.05, or 0.055 The tolerable size of the strain discontinuity is controlled using $t_2$ to provide the desired strain contrast. Accordingly, $t_2$ is usually chosen to be 40% of the largest possible strain value (i.e., the applied physical compression). In the above example $t_2$ is 0.4*0.05, or 0.02. Spikes, or local isolated computational noise spots, are accounted for using $t_3$. Through experimentation, it was found that such spikes larger than 0.0015 are noticeable. Therefore, $t_3$ is typically set to 0.0015. All nodes with a goodness measure value of 0 are discarded. The remaining nodes are then used to interpolate or extrapolate the discarded node locations.

As shown in FIG. 6, in module D, an energy function is defined and minimized. The energy function E allows the displacement of each signal between the first and second data sets to be tracked. The energy function has two components. The deforming energy tends to deform the mesh towards the best match between the two image frames; while the resisting energy maintains the elasticity properties of the mesh. Noise is kept low by balancing the matching and smoothing operations. In this manner, shearing and rotation may be detected.

E is an energy function defined as:

$$E = \sum_{p \in P} E_m(p) + \beta \sum_{n' \in N'} E_d(n') \quad (6)$$

where p and n' are the above defined sets of all patches and deformed nodes, respectively; $E_m(p)$ is the matching energy between the patches p and p'; $E_d(n')$ is the dispersion energy of the deformed node n'; and β is a constant chosen to balance the relative weight of $E_m$ and $E_p$.

R(p) represent all signals in initial patch p. The matching energy is defined as:

$$E_m(p) = \sum_{U(x,y) \in R(p)} [U(x, y) - C(x', y')]^2 \quad (7)$$

where (x', y') is the bilinear-transformed coordinate of (x, y). In the preferred embodiment, the matching error is calculated as the sum of the squared differences between all signals in an initial patch and its deformed counter-part. Let $(x_n', y_n')$ and $(x_{np}', y_{np}')$ be the location of the displaced node n' and its predicted location, respectively. The dispersion energy is defined as:

$$E_d(n') = \exp\left(\sqrt{(x'_n - x'_{np}) + (y'_n - y'_{np})}\right) \quad (8)$$

The location of the displaced node n' is ascertained by calculating the x coordinate in the following way. First, the x coordinate for five columns of nodes are averaged as:

$$\bar{x}_i = \frac{\sum_{j=-2}^{2} g([i, n'_2 + j]) L_x([i, n'_2 + j])}{5} \quad (9)$$

for $i = n'_1 - 2, n'_1 - 1, \ldots, n'_1 + 2$

Then a linear regression algorithm defined as:

$$x(i) = \alpha \times i + b \quad (10)$$

is used to fit i and x(i) to a line. Finally, the predicted x coordinate is found as:

$$x(n'_1) = a \times n'_1 + b \quad (11)$$

The predicted value of the coordinate of n' is found in the same way.

Next, as shown in FIG. 6, the total energy function E is minimized. Generally, Warping the signals in U to give the minimum mean-squared difference between W and C reduces the matching error. If the motion is too great, C will be decorrelated from U and noise rather than the true displacement may determine the best signal value match. For such a case, the second term, dispersion energy, is introduced. Next, because biological tissues are generally elastic, it is assumed that biological tissue under compression is incompressible and deforms continuously, i.e., Poisson's ratio is approximately 0.5. Minimizing the energy function $E_m$ provides a force to drag the mesh nodes to the locations that provide the best signal match. $E_d$ provides a force that resists the unreasonably large, local nodal displacements encouraged by $E_m$ in cases where U and C are decorrelated. In other words, $E_d$ is a smoothness constraint. Creating an equilibrium state between these two forces minimizes the total energy.

As shown in FIG. 4 and FIG. 5, the energy minimization method is employed as follows. Each node of the deformable mesh is perturbed to its eight neighboring locations and the energy function value for each location is computed. Each node is then moved to the location that produces the lowest energy function value as shown in FIG. 5. This process is repeated until no further energy reduction can be achieved by further perturbing the nodal locations. It is to be noted that by definition, the energy function value is always non-negative. Further, each energy function value upgrade lowers the energy functions current value. Because the nodes only take integer locations, there is a finite number of mesh configurations and the convergence of the minimization algorithm is guaranteed. Approximately five to seven iterations of the minimization algorithm are required to reach convergence.

Several techniques may be employed to speed up the computations involved in the minimization process. Bilinear transformation results may be rounded to the closest integer values because sub-sample displacement is estimated with cross correlation. Additionally, because perturbing one node on the deformed mesh only changes four patches at most (two patches on the border, one on the corners), after calculating the initial energy function value between initial and deformed meshes, only four (sometimes two or one) patches need to be computed again when perturbing a node. Thus, the energy function value can be upgraded by subtracting the difference provided by these four (two or one) patches between iterations i and i+1.

It is possible that the chosen size of the mesh patches is so large that it effects the quality of the resulting strain image. Larger patch sizes provide precise nodal displacement estimates because there are more signals to compare. Smaller patch sizes, however, provide a lower precision, but higher spatial resolution. It is preferred to identify the optimal patch size, by minimizing the energy function multiple times with the patch size decreased on successive iterations until the patch size is small enough. In the preferred embodiment, the patch size is split evenly on both the initial and deformed mesh, e.g., from approximately 64×4 to approximately 32×2 to approximately 16×1. Finally, the Warped first data set is created in module F through the application of the bilinear transformation.

Next, as shown in FIG. 7, any residual axial displacement is estimated by performing one dimensional cross correlation of the second data set and the Warped first data set. Then, the total displacement field is found by summing the displacement accounted for in warping and the output of the cross correlator. The strain image is then formed by taking the gradient of the total displacement field along the ultrasound beam and displaying that gradient on a PC monitor or any special purpose video hardware.

3-D Local Linear Warping

When the biological tissue being scanned is fairly homogeneous and not overly complex, like breast tissue in a young patient or early stage cancer, compensating for rotational motion and shear is not necessary. The presence of complex biological tissue can frequently be detected by examining the ultrasound scan while recording the pre and post-compression echo fields. In this case, a more computationally efficient version of Warping called 3-D Local Linear Warping is used. 3-D Local Linear Warping only accounts for translational motion and scaling of the biological tissue in any direction, including out of plane displacement.

As shown in FIG. 1, a transducer having a rectangular grid of sensors is flush mounted to a planar compressor surface. While a two dimensional planar array transducer is preferred, a transducer having sensors in concentric circles or a linear array transducer may be used.

In the preferred embodiment, the planar array transducer is an f/2 system with an A-line density of 5 per millimeter and emits broadband ultrasonic waves with a center frequency of 5 MHz and a bandwidth of 4 MHz and records 200 echo waveforms for a 40 mm×40 mm region at a sampling rate of 45 samples per second. While this is preferred, any acceptable transmission/recording specifications may be used. Also, while the 3-D Local Linear Warping technique is described in a preferred embodiment in conjunction with ultrasound, 3-D Local Linear Warping may also be used to improve image quality in magnetic resonance imaging, x-ray imaging and other electromagnetic diagnostic imaging techniques.

As shown in FIG. 1, the planar compressor is mounted in the x, y plane to be in contact with the biological tissue. While it is preferred to use a planar compressor, the transducer, a human hand, or any suitable device may serve to maintain an axial compression on the target object. As shown in FIG. 2, the compressor may be moved along the z-axis by a computer controlled stepper motor having it's position monitored by an optical encoder.

As shown in FIG. 2, the transducer is preferably connected for the purpose of signal processing and image formation to a DEC Alpha workstation, although any general-purpose computer and monitor may be used. Signal processing and image formation is conducted off-line on the computer, although such processing could be conducted on-line by using any dedicated system such as a digital signal processor. As shown in FIG. 1, the transducer scans the biological tissue for a pre-compression image by emitting ultrasonic pulses that travel through the biological tissue. These ultrasonic pulses are scattered within the biological tissue and the back-scattered energy is recorded by the sensors in the transducer and stored in the processing computer as A-lines. This group of A-lines combines to form the first data set. Thus, the pre-compression echo field is stored as the first data set in the computer for later processing.

Next, as shown in FIG. 7, an axial compression is applied to the biological tissue. Compressions up to 10% of the biological tissue's height may be applied to obtain better contrast in the strain image. The user inputs a desired compression into the computer, which passes along the instruction to the computer-controlled stepper motor. The computer controlled stepper motor in turn moves the planar compressor along the z-axis to compress the biological tissue the desired amount. After compression, the transducer scans for a post-compression image generating a second data set in the same manner as the first data set.

It is preferred to employ a two-dimensional detector array; although a one-dimensional array may be used. If only a one dimensional detector array is available, a plurality of pre-compression images may be taken to obtain the required three dimensional data set from the biological tissue. All the data from multiple pre-compression scans is then combined to form the first data set. In 3-D Local Linear Warping, only one post-compression scan plane, forming a two-dimensional second data set, is taken. Again, while it is preferred to warp the first data set to account for the physical deformation in the second data set, it is acceptable to warp the second data set to remove this deformation.

Figure 8:
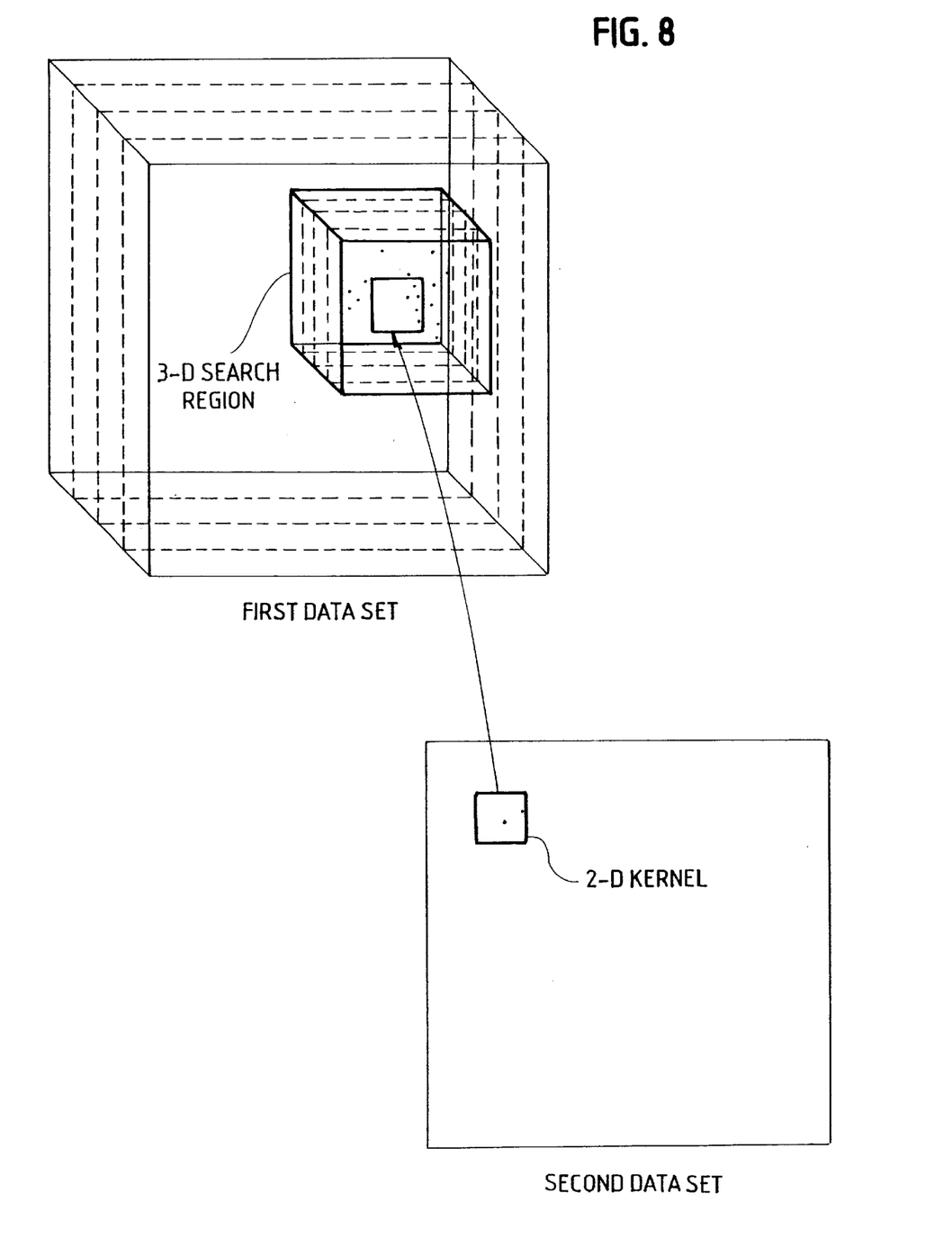
FIG. 8 is a representation of a two dimensional data kernel selected in a second data set and compared to data in a three dimensional search region of the first data set.
Figure 9:
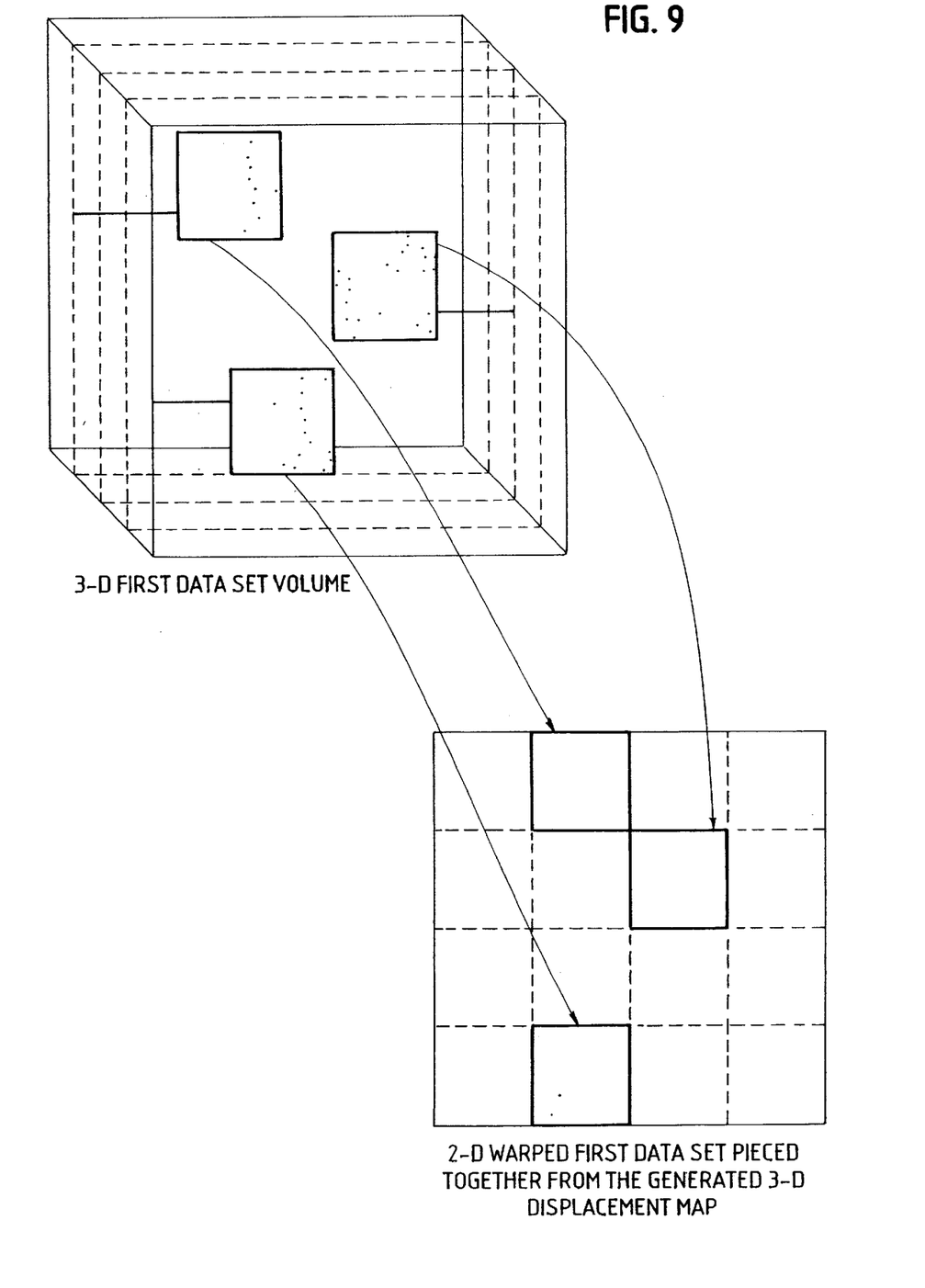
FIG. 9 is a representation of the 2-D warped data set pieced together from the generated 3-D displacement map.

A high level view of the entire image creation process is shown in FIG. 7. Once the first and second data sets are stored, 3-D Local Linear Warping is performed. First, a two dimensional mesh is created on the second data set. Second, each A-line in second data set is stretched by the amount of compression applied. Third, as shown in FIG. 8, a two-dimensional data kernel is selected in the second data set and compared to data in a three-dimensional search region of the first data set. Search regions are selected from the geometry and the amount of compression used. The displacement for each pixel is calculated using a block matching algorithm. While any block matching algorithm may be used, the Sum Absolute Difference (SAD) algorithm is preferred for computational efficiency. Accordingly, the minimum SAD locations are measured for each sample in the first data set to find a three-dimensional displacement map that describes the physical deformation. From this displacement map, as shown in FIG. 9, a two dimensional pre-compression image is pieced together from the first data set so that the result is deformed similar to the physical compression.

Next, any residual axial displacement is estimated by performing one dimensional cross correlation between the second data set and the 3-D Locally Linear Warped first data set. Finally, the total displacement field is found by summing the displacements accounted for during Warping and the residual displacement estimated with the cross correlator. The strain image is then formed by taking the gradient of the total displacement field along the ultrasound beam and displaying that gradient on a PC monitor or any special purpose video hardware.

2.5-D Local Linear Warping

When the motion of the biological tissue to be scanned is appropriately naturally constrained by a bone or other internal structure, the motion can be assumed to be in a plane different from but approximately parallel to the ultrasound scan plane, and 2.5-D Local Linear Warping can be used. 2.5-D Local Linear Warping is effective when all data in a single pre-compression plane generally moves to a single post-compression scan planes.

As shown in FIG. 1, a transducer having a rectangular grid of sensors is flush mounted to a planar compressor surface. While a two dimensional planar array transducer is preferred, a transducer having sensors in concentric circles or a linear array transducer may be used.

In the preferred embodiment, the planar array transducer is an f/2 system with an A-line density of 5 per millimeter and transmits broadband ultrasonic waves with a center frequency of 5 MHz and a bandwidth of 4 MHz and records 200 echo waveforms for a 40 mm×40 mm region at a sampling rate of 45 samples per second. While this is preferred, any acceptable transmission/recording specifications may be used. Also, while the 2.5-D Local Linear Warping technique is described in a preferred embodiment in conjunction with ultrasound, 2.5-D Local Linear Warping may also be used to improve image quality in magnetic resonance imaging, x-ray imaging and other electromagnetic diagnostic imaging techniques.

As shown in FIG. 1, the planar compressor is mounted in the x, y plane to be in contact with the biological tissue depicted as a gelatin phantom. While it is preferred to use a planar compressor, the transducer, a human hand, or any suitable device may serve to maintain an axial compression on the biological tissue. As shown in FIG. 2, the compressor may be moved along the z-axis by a computer controlled stepper motor having it's position monitored by an optical encoder.

As shown in FIG. 2, the transducer is preferably connected for the purpose of signal processing and image formation to a DEC Alpha workstation, although any general-purpose computer and monitor may be used. Signal processing and image formation is conducted off-line on the computer, although such processing could be conducted on-line by using any dedicated system such as a digital signal processor. As shown in FIG. 1, the transducer scans the biological tissue for a pre-compression image by emitting ultrasonic pulses that travel through the biological tissue depicted as a gelatin phantom. These ultrasonic pulses are scattered within the biological tissue and the back-scattered energy is recorded by the sensors in the transducer and stored in the processing computer as A-lines. This group of A-lines combines to form the first data set. Thus, a three dimensional pre-compression echo field is stored as the first data set in the computer for later processing.

Next, as shown in FIG. 7, an axial compression is applied to the biological tissue. Compressions up to 10% of the biological tissue's height may be applied to obtain better contrast in the strain image. The user inputs a desired compression into the computer, which passes along the instruction to the computer-controlled stepper motor. The computer controlled stepper motor in turn moves the planar compressor along the z-axis to compress the biological tissue the desired amount. After compression, the transducer scans for a post-compression image generating a second data set in the same manner as the first data set.

It is preferred to employ a two-dimensional detector array; although a one-dimensional array may be used. If only a one dimensional detector array is available, a plurality of pre-compression images may be taken to obtain the required three dimensional data set from the target object. All the data from the multiple pre-compression scans is then combined to form the first data set. In 2.5-D Local Linear Warping, only one post-compression scan plane, forming a two-dimensional second data set, is taken. Again, while it is preferred to warp the first data set to account for the physical deformation in the second data set, it is acceptable to warp the second data set to remove this deformation.

Figure 10:
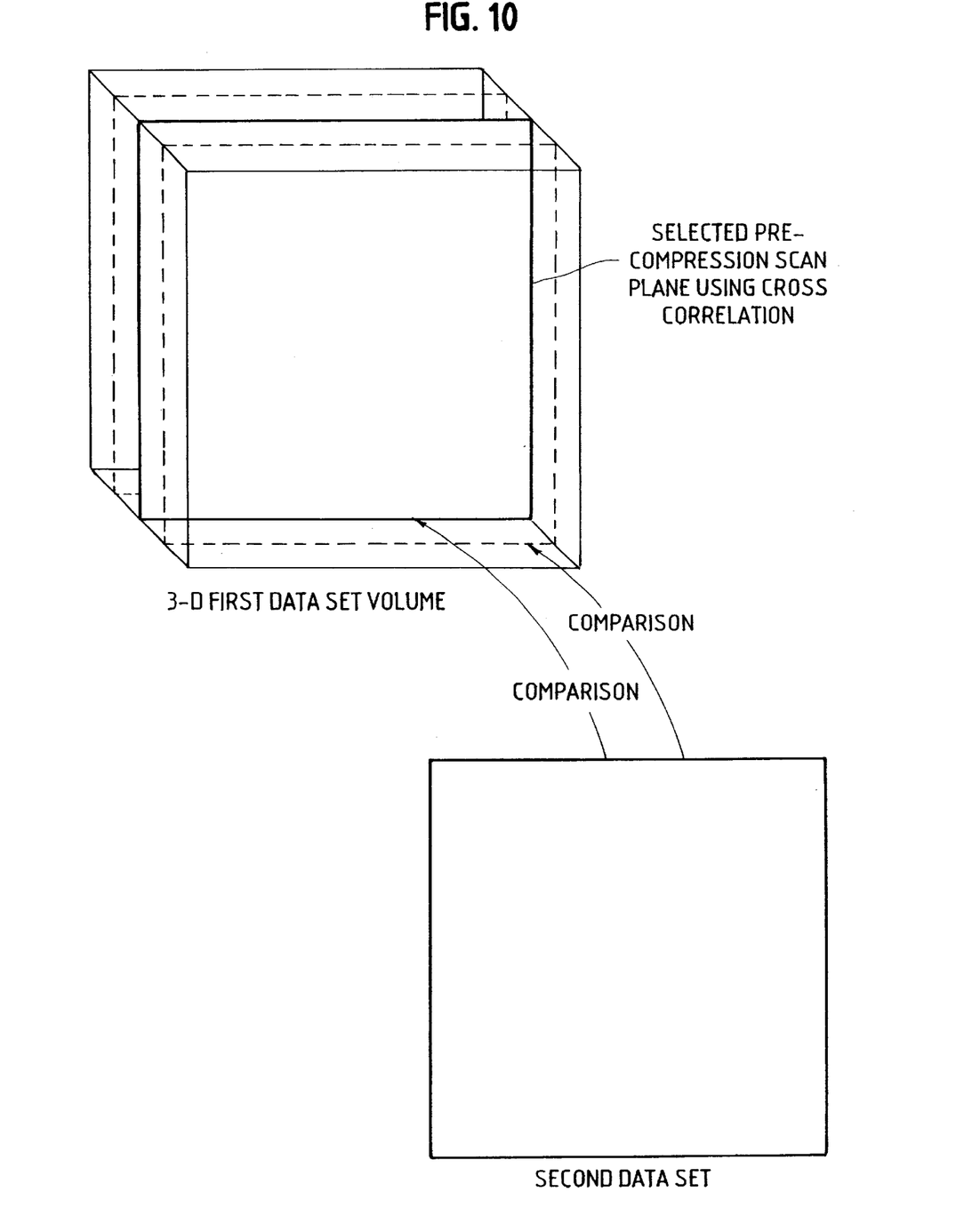
FIG. 10 is a representation of the selected pre-comparison scan plane using cross correlation.

A high level view of the entire image creation process is shown in FIG. 7. Once the first and second data sets are stored, 2.5-D Local Linear Warping is performed. First, a two dimensional mesh is created on the second data set. Second, each A-line in the second data set is stretched by the amount of applied compression. Third, as shown in FIG. 10, the pre-compression scan plane from which data has moved to the acquired post-compression scan plane is identified by two dimensional cross correlating the post-compression scan plane with each of the pre-compression scan planes. Next, a two-dimensional data kernel is selected in the second data set and compared to data in a two-dimensional search region of the previously identified pre-compression scan plane in the first data set. Then, the local displacement for each pixel is calculated using a block matching algorithm. While any block matching algorithm may be used, the Sum Absolute Difference algorithm is preferred for computational efficiency. Accordingly, the first data set is deformed such that the deformation in the resulting echo field is similar to the physical compression recorded in the second data set and 2.5-D Local Linear Warping is complete. The total displacement field is found by summing the displacement applied to the first data set during 2.5-D Local Linear Warping and the fine scale displacement estimated subsequently from cross correlation. The strain image is then formed by taking the gradient of this total displacement field along the ultrasound beam and displaying that gradient on a PC monitor or any special purpose video hardware.

2-D Local Linear Warping

When no naturally occurring constraint exists, but the motion of the biological tissue to be scanned can be artificially restricted to the ultrasound plane by the imposition of any suitable physical boundary conditions, like breast tissue constrained by two Plexiglas plates, then 2-D Local Linear Warping is used. Because the motion is confined to a single plane, only single scan planes need be recorded for both pre and post-compression.

As shown in FIG. 1, a transducer having a rectangular grid of sensors is flush mounted to a planar compressor surface perpendicular to the constraining plates. While a two dimensional planar array transducer is preferred, a transducer having sensors in concentric circles or a linear array transducer may be used.

In the preferred embodiment, the planar array transducer is an f/2 system with an A-line density of 5 per millimeter and emits broadband ultrasonic waves with a center frequency of 5 MHz and a bandwidth of 4 MHz and records 200 echo waveforms for a 40 mm×40 mm region at a sampling rate of 45 samples per second. While this is preferred, any acceptable transmission/recording specifications may be used. Also, while the 2-D Local Linear Warping technique is described in a preferred embodiment in conjunction with ultrasound, 2-D Local Linear Warping may also be used to improve image quality in magnetic resonance imaging, x-ray imaging and other electromagnetic diagnostic imaging techniques.

As shown in FIG. 1, the planar compressor is mounted in the x, y plane to be in contact with the biological tissue depicted as a gelatin phantom. While it is preferred to use a planar compressor, the transducer, a human hand, or any suitable device may serve to maintain an axial compression on the biological tissue. As shown in FIG. 2, the compressor may be moved along the z-axis by a computer controlled stepper motor having its position monitored by an optical encoder.

As shown in FIG. 2, the transducer is preferably connected for the purpose of signal processing and image formation to a DEC Alpha workstation, although any general-purpose computer and monitor may be used. Signal processing and image formation is conducted off-line on the computer, although such processing could be conducted on-line by using any dedicated system such as a digital signal processor. As shown in FIG. 1, the transducer scans the biological tissue, depicted as a gelatin phantom, for a two dimensional pre-compression echo field by transmitting ultrasonic pulses that travel through the biological tissue. These ultrasonic pulses are scattered within the biological tissue and the back-scattered energy is recorded by the sensors in the transducer and stored in the processing computer as A-lines. This group of A-lines combines to form the first data set. Thus, the pre-compression echo field is stored as the first data set in the computer for later processing.

Next, as shown in FIG. 7, an axial compression is applied to the biological tissue. Compressions up to 10% of the biological tissue's height may be applied to obtain better contrast in the strain image. The user inputs a desired compression into the computer, which passes along the instruction to the computer-controlled stepper motor. The computer controlled stepper motor in turn moves the planar compressor along the z-axis to compress the biological tissue the desired amount. After compression, the transducer scans for a post-compression echo field generating a second data set in the same manner as the first data set. While it is preferred to warp the first data set to account for the physical deformation in the second data set, it is acceptable to warp the second data set to remove this deformation.

A high level view of the entire image creation process is shown in FIG. 7. Once the first and second data sets are stored, 2-D Local Linear Warping is performed. First, a two dimensional mesh is created on the second data set. Second, each A-line in the second data set is stretched by the amount of applied compression. Third, a two-dimensional data kernel is selected in the second data set and compared to data in a two-dimensional search region of the pre-compression scan plane in the first data set. Then, the local displacement for each pixel is calculated using a block matching algorithm. While any block matching algorithm may be used, the Sum Absolute Difference algorithm is preferred for computational efficiency. Accordingly, the first data set is deformed such that the deformation in the resulting echo field is similar to the physical compression recorded in the second data set and 2-D Local Linear Warping is complete. The total displacement field is found by summing the displacement applied to the first data set during 2-D Local Linear Warping and the fine scale displacement estimated subsequently with cross correlation. The strain image is then formed by taking the gradient of this total displacement field along the ultrasound beam and displaying that gradient on a PC monitor or any special purpose video hardware.

Global Warping methods may be applied prior to the finer process of Local Warping described above in all methods presented to increase processing speed but will not improve image quality and are, therefore, not necessary.

The foregoing description and drawings merely explain and illustrate the invention and the invention is not limited thereto. Those of the skill in the art who have the disclosure before them will be able to make modifications and variations therein without departing from the scope of the present invention.

What is claimed is:

1. A method for motion estimation within biological tissue comprising:

(a) acoustically coupling a transducer to a target biological tissue;

(b) emitting at least one ultrasonic signal from said transducer into said target tissue along a scan plane;

(c) collecting ultrasonic energy back-scattered by at least said target biological tissue;

(d) storing said back-scattered ultrasonic energy collected in step (c) as a first data set;

(e) compressing said target biological tissue in a substantially axial direction;

(f) emitting at least one ultrasonic signal from said transducer into said target tissue along said scan plane while substantially maintaining said compression;

(g) collecting ultrasonic energy back-scattered by at least said target biological tissue under said compression;

(h) storing said back-scattered ultrasonic energy collected in step (g) as a second data set;

(i) warping one of said first and second data sets to account for said compression to form a warped data set;

(j) cross-correlating said warped data set with the unwarped one of said first and said second data sets to obtain a fine scale displacement of said target biological-tissue from the displacement estimated by said warping.

(k) summing said fine scale displacement and said warped data set to obtain a total axial displacement;

(l) taking a gradient of said total axial displacement; and (m) forming a strain image from said gradient of said total axial displacement.

* * * * *

UNITED STATES PATENT AND TRADEMARK OFFICE
CERTIFICATE OF CORRECTION

PATENT NO.    : 6,277,074 B1
DATED         : August 21, 2001
INVENTOR(S)   : Chaturvedi et al.

It is certified that error appears in the above-identified patent and that said Letters Patent is hereby corrected as shown below:

Column 2,
Line 18, delete "1 -D" and insert -- 1-D -- therefor.

Column 11,
Line 26, insert "y" between "the" and "coordinate".

Column 18,
Line 17, delete "-" between "biological" and "tissue".
Line 18, delete "." and insert -- ; -- therefor.

Signed and Sealed this

Thirtieth Day of April, 2002

Attest:

JAMES E. ROGAN
Director of the United States Patent and Trademark Office

Attesting Officer